July 12, 1949. E. S. BOERNER Plant Pat. 852
ROSE PLANT
Filed Jan. 5, 1948
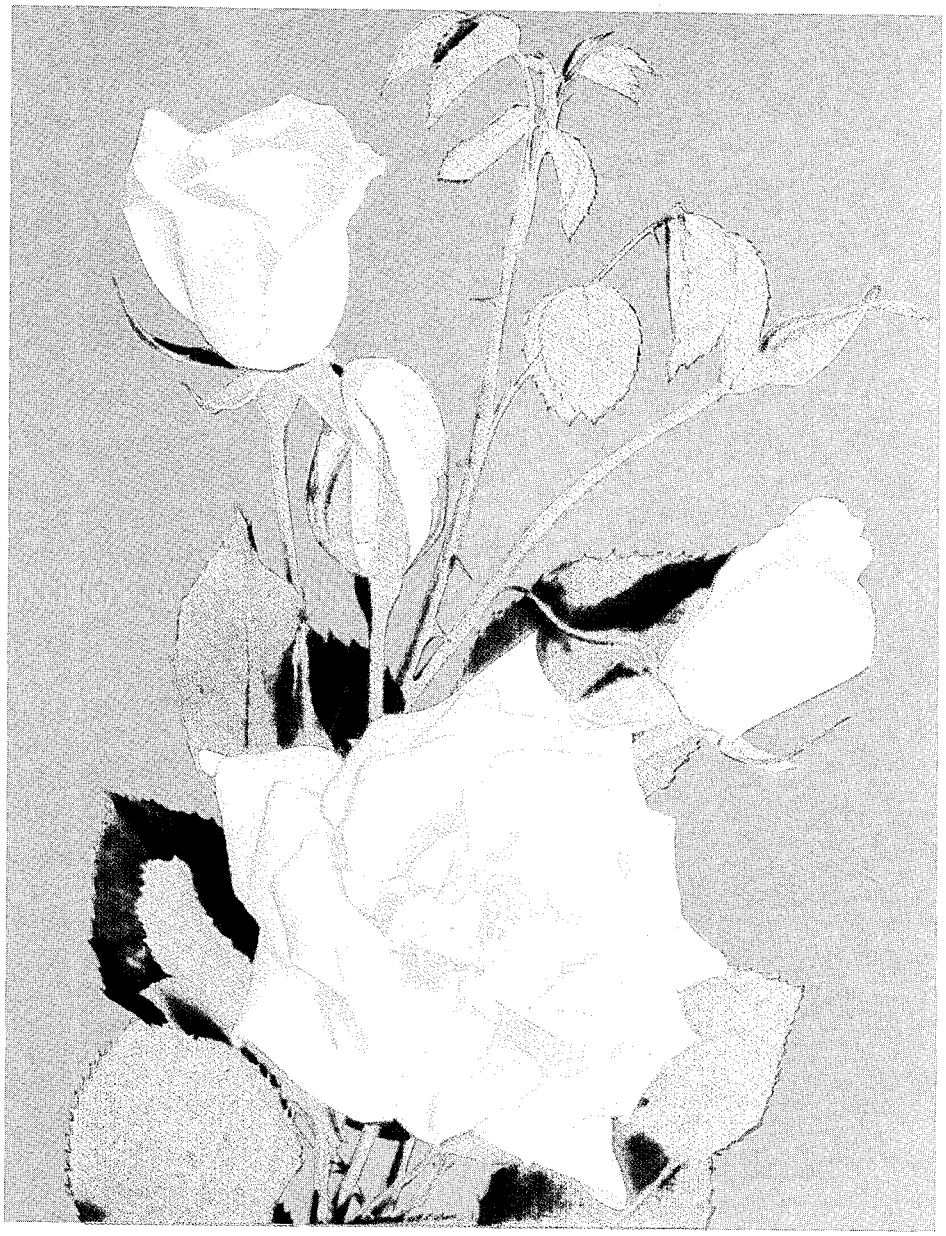
Inventor
E. S. Boerner
By Robb & Robb
Attorneys Patented July 12, 1949

UNITED STATES PATENT OFFICE

852

ROSE PLANT

Eugene S. Boerner, Newark, N. Y., assignor to Jackson & Perkins Company, Newark, N. Y., a corporation of New York Application January 5, 1948, Serial No. 497

1 Claim. (Cl. 47—61)

The present invention relates to a new and distinct variety of rose plant, produced by crossing two well known varieties for the purpose of combining as many of their good characteristics as possible in the progeny.

The new variety is characterized as to novelty by the dominant and definitely distinctive pink coloring of its flowers; the unusally great production of flowers in the greenhouse for a rose of this color; the habit of the flower of opening in a cupped form and finishing in a flat form, thereby becoming an easily recognizable rose; and the distinctive green color of the young foliage with red serrations.

These characteristics come true to form in asexual reproductions.

In the accompanying drawing is shown specimens of the rose, including the young foliage and flowers in different stages of development from bud to full blown flower.

The following is a detailed description of the new variety, color terminology being in accordance with Ridgway's Color Standards and Nomenclature:

Parentage: Seedling.

*Seed parent.*—"Sonata," Pl. Pat. #732.

*Pollen parent.*—"R. M. S. Queen Mary," Pl. Pat. #249.

Classification: Botanic and commercial—hybrid tea.

*Flower*

Blooming habit: Recurrent—continuous.

Location where observations were made—Newark, New York, in the morning in the month of September.

Bud:

*Size.*—Medium.

*Form.*—Pointed. Is not affected by wet or hot weather.

*Color.*—When sepals first divide—Eugenia Red, Plate 13. When petals being to unfurl—Rose Doree, Plate 1. When half blown—inside of petals—Flesh color, Plate 14; Reverse of petals—Strawberry Pink, Plate 1, overcast with Light Jasper Red, Plate 13.

*Sepals.*—Branched. Curl back when petals begin to unfurl. Color—Inside—Lumiere Green, Plate 17. Outside—Parrot Green, Plate 6.

*Calyx.*—Shape—Pear. Size—Small. Aspect—Smooth. Odor when rubbed—None. Color—Lettuce Green, Plate 5.

*Peduncle.* — Length — Medium. Aspect — Smooth. Color—Lettuce Green, Plate 5. Strength—Erect; slender.

*Opening.*—Bud opens up well. Is not affected by adverse weather conditions.

Bloom:

*Size.*—Large. Average size when fully expanded—4½".

*Borne.*—Singly and several together.

*Stems.*—Long; strong.

*Form.*—When first open—cupped. Permanence—flattens.

*Petalage.*—Double (full but open center). Number of petals under normal conditions, 25.

*Color.*—Center of flower—Grenadine Pink, Plate 2, overcast with La France Pink, Plate 1. Outer petals—Safrano Pink, Plate 2. Base of petals (aiglet)—Light Cadmium, Plate 4. Inside of petals—La France Pink, Plate 1, tinted with Orient Pink, Plate 2. Reverse of petals—Geranium Pink, Plate 1, overcast with La France Pink, Plate 1. General tonality from a distance—Grenadine Pink, Plate 2, overcast with Safrano Pink, Plate 2.

*Discoloration.*—At end of first day—Grenadine Pink, Plate 2, overcast with Safrano Pink, Plate 2. Second day—Grenadine Pink, Plate 2, overcast with Shrimp Pink, Plate 1. Third day—La France Pink, Plate 1, tinted with Orient Pink, Plate 2.

Petals:

*Texture.*—Thick. Is not affected by wet or hot weather.

*Appearance.*—Inside — satiny; outside—shiny.

*Form.*—Pointed.

*Arrangement.*—Imbricated (regularly arranged shingle-like). Petaloids in center—few; small.

*Persistence.*—Drop off cleanly.

*Fragrance.*—Moderate. Nature—"Old Rose perfume" (Centifolia).

*Lasting quality.*—On the plant and as cut flower—long.

Genital organs:

*Stamens.*—Anthers—large; many. Color—Capucine Yellow, Plate 3. Arrangement—regular around styles.

*Stamens.* — Filaments — long. — Color—Spectrum Red, Plate 1.

*Pollen.*—Orange Buff, Plate 3.

*Styles.*—Bunched uneven length; medium length; thin.

*Stigmas.*—Maize Yellow, Plate 4.
*Ovaries.*—All enclosed in calyx.

*Plant*

Form: Bush.
Growth: Vigorous; upright.
Foliage: 3 to 5 leaflets.
*Size.*—Large.
*Quantity.*—Abundant.
*Color.*—New foliage: upper side—Parrot Green, Plate 6, serrations Oxblood Red, Plate 1; under side—Yellowish Oil Green, Plate 5, serrations Oxblood Red, Plate 1. Old foliage: upper side—Dark Cress Green, Plate 31; under side—Light Elm Green, Plate 17.
*Shape.*—Oval pointed.
*Texture.*—Upper side—leathery; glossy; under side—rough. Ribs and veins—ordinary.
*Edge.*—Serrated (saw toothed).
*Serration.*—Single; small.
*Leaf stem.*—Color—Mignonette Green, Plate 31. Under side—prickles.
*Stipules.*—Medium length; smooth.
*Disease resistance.*—Resistant.

Wood:
*New wood.*—Color—Russet, Plate 15. Bark—smooth.
*Old wood.*—Color—Light Cress Green, Plate 31. Bark—smooth.
Thorns:
*Thorns.*—Quantity on main stalks from base and on laterals from stalk—ordinary. Form—narrow base; medium length; hooked downward. Color when young—Carmine, Plate 1. Position—irregular.
*Prickles.*—Quantity on main stalks and on laterals—few. Color—Old Rose, Plate 13.
*Short needles.*—Quantity on main stalks and on laterals—none.

I claim:

A new and distinct variety of hybrid tea rose plant characterized as to novelty by the coloring of the flowers; floriferousness, especially unusual production of flowers in greenhouse; the habit of the flowers of opening in a cupped form and finishing in flat form; and the coloring of the foliage, substantially as shown and described.

EUGENE S. BOERNER.

No references cited.